United States Patent
Dosa et al.

(10) Patent No.: US 9,580,459 B2
(45) Date of Patent: Feb. 28, 2017

(54) WATER-SOLUBLE URSODEOXYCHOLIC ACID PRODRUGS

(71) Applicant: Metselex, Inc., Minneapolis, MN (US)

(72) Inventors: Peter Ian Dosa, Vadnais Heights, MN (US); Clifford John Steer, Eagan, MN (US); Ingrid Gunda Georg, St. Paul, MN (US)

(73) Assignee: Metselex, Inc., Minneapolis, MN (US)

( * ) Notice: Subject to any disclaimer, the term of this patent is extended or adjusted under 35 U.S.C. 154(b) by 0 days.

(21) Appl. No.: 14/261,963

(22) Filed: Apr. 25, 2014

(65) Prior Publication Data

US 2014/0323748 A1 Oct. 30, 2014

Related U.S. Application Data

(60) Provisional application No. 61/816,204, filed on Apr. 26, 2013.

(51) Int. Cl.
*C07J 51/00* (2006.01)

(52) U.S. Cl.
CPC .................................... *C07J 51/00* (2013.01)

(58) Field of Classification Search
CPC ...................................................... C07J 51/00
See application file for complete search history.

(56) References Cited

U.S. PATENT DOCUMENTS 6,451,776 B2 * 9/2002 Stella ..................... A61K 38/13
  514/119
6,992,076 B2 * 1/2006 Cundy ................... A61K 31/56
  514/182

OTHER PUBLICATIONS

Zaragoza Dorwald, Side Reactions in Organic Synthesis, 2005, Wiley-VCH Verlag GmbH & Co. KGaA, Weinheim, Preface. p. IX.*
Elder et al, Journal of Pharmaceutical Sciences, The Utility of Sulfonate Salts in Drug Development ,2010, 99(7), pp. 2948-2961.*
Sittig, Pharmaceutical Manufacturing Encyclopedia, 1988, Noyes Publications, Westwood, NJ, pp. v.-1756.*
Muhammad Safadi, Reza Oliyai, and Valentino J. Stella, Phosphoryloxymethyl Carbamates and Carbonates—Novel Water-Soluble Prodrugs for Amines and Hindered Alcohols, Mar. 2, 1993, 6 pages, Pharmaceutical Research, vol. 10, No. 9, 1993.

* cited by examiner

*Primary Examiner* — Paul A Zucker
(74) *Attorney, Agent, or Firm* — Kinney & Lange, P.A.

(57) ABSTRACT

Ursodeoxycholic acid (UDCA) is a bile acid with demonstrated anti-apoptotic activity in both in vitro and in vivo models. Water-soluble prodrugs of UDCA for use in indications where intravenous administration of UDCA may be preferable, such as reducing damage from stroke or acute kidney injury, are disclosed. The disclosed prodrugs showed significant anti-apoptotic activity in a series of in vitro assays.

7 Claims, 10 Drawing Sheets

Chemical stability of different salt forms of compound 19

| Compound | Counterion | Equiv. | %Remaining[a] |
|---|---|---|---|
| 19b | Tris | 2 | 36 |
| 19c | Isopropylamine | 2 | 34 |
| 19d | Tris | 1 | 88 |
| 19e | Tris | 3 | 33 |

[a] Percent of prodrug remaining after seven days at room temperature in $D_2O$ solution. n = 3; standard deviation < 2%.

Fig. 10

WATER-SOLUBLE URSODEOXYCHOLIC ACID PRODRUGS

CROSS-REFERENCE TO RELATED APPLICATION

This patent application claims priority to U.S. Application No. 61/816,204, filed on Apr. 26, 2013 and entitled "WATER-SOLUBLE PRODRUGS OF THE ANTI-APOPTOTIC BILE ACID UDCA", which is hereby incorporated by reference in its entirety.

BACKGROUND

Ursodeoxycholic acid (UDCA) is a naturally occurring component of bile used clinically to treat primary biliary cirrhosis. In addition to treating various other liver diseases, UDCA and its taurine-conjugated derivative tauroursodeoxycholic acid (TUDCA) are anti-apoptotic agents that are known to have protective effects in animal models of multiple disorders including Huntington's disease, spinal cord injury, cataracts, and acute pancreatitis. The molecular mechanisms underlying the cytoprotective activities of these molecules are believed to engage a number of different pathways including preventing Bax-induced membrane perturbation in mitochondria, blocking caspase-3 activation, inhibiting calpain and caspase-12 activation caused by ER stress, and by modulating miRNA gene regulation.

SUMMARY

The present disclosure describes the synthesis of highly water-soluble prodrugs of UDCA. A first aspect of this disclosure relates to synthesizing phosphate ester prodrugs to increase aqueous solubility by several orders of magnitude.

BRIEF DESCRIPTION OF THE DRAWINGS

FIG. 10 shows the chemical stability of different forms of compound 19.

DETAILED DESCRIPTION

As used herein, "pharmaceutically acceptable salts" refers to derivatives of the disclosed compounds where the parent compound is modified by converting an existing acid or base moiety into its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the present invention include the conventional non-toxic salts or the quaternary ammonium salts of the parent compound formed, for example, from non-toxic inorganic or organic acids. Pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two.

As used herein, "prodrugs" refer to any covalently bonded carriers which release the active parent drug when administered to a subject. Prodrugs can be prepared by modifying functional groups present in the compounds in such a way that the modifications are cleaved, either in routine manipulation or in vivo, to the parent compounds.

Figure 1:
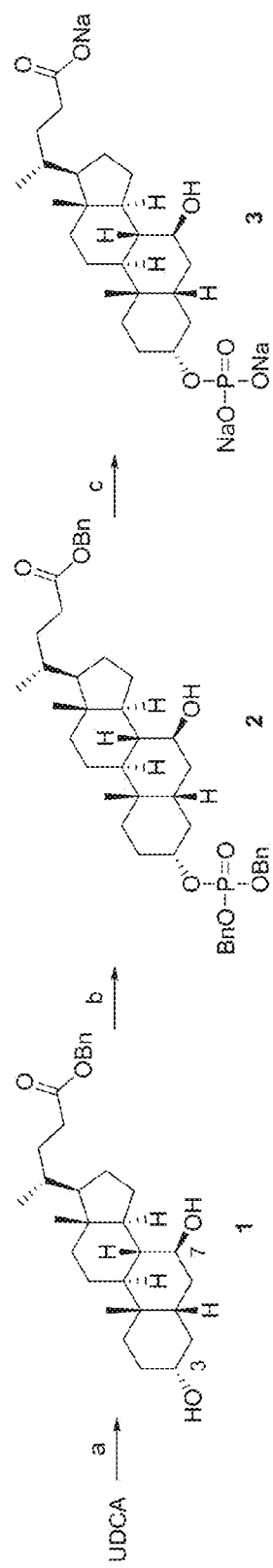
FIG. 1 illustrates synthesis of a 3-substituted phosphate prodrug (compound 3).

Ursodeoxycholic acid (UDCA) has two alcohol moieties to which a phosphate can be directly attached, located at the 3- and 7-positions. As shown in FIG. 1, synthesis of these prodrug compounds begins by benzyl protecting the acid of UDCA, which proceeded in high yield using benzyl bromide as the alkylating agent. Heating the resulting benzyl ester (compound 1) with dibenzyl N,N-diethylphosphoramidite followed by oxidation with $H_2O_2$ furnished a phosphate ester (compound 2), the structure of which was confirmed by NMR spectroscopy. Removal of the three benzyl groups of compound 2 using hydrogen and Pd/C followed by treatment with sodium carbonate yielded the desired 3-substituted phosphate ester prodrug of UDCA (compound 3). Reagents and conditions included: (a) benzyl bromide, $K_2CO_3$, acetonitrile, 80° C.; (b) i. dibenzyl N,N-diethylphosphoramidite, 1,2,4-triazole, $NaHCO_3$, 1,2-dichloroethane, 65° C., ii. 30% $H_2O_2$, 0° C.; and (c) i. Pd/C, $H_2$, methanol, ii. Na2CO3.

Figure 2:
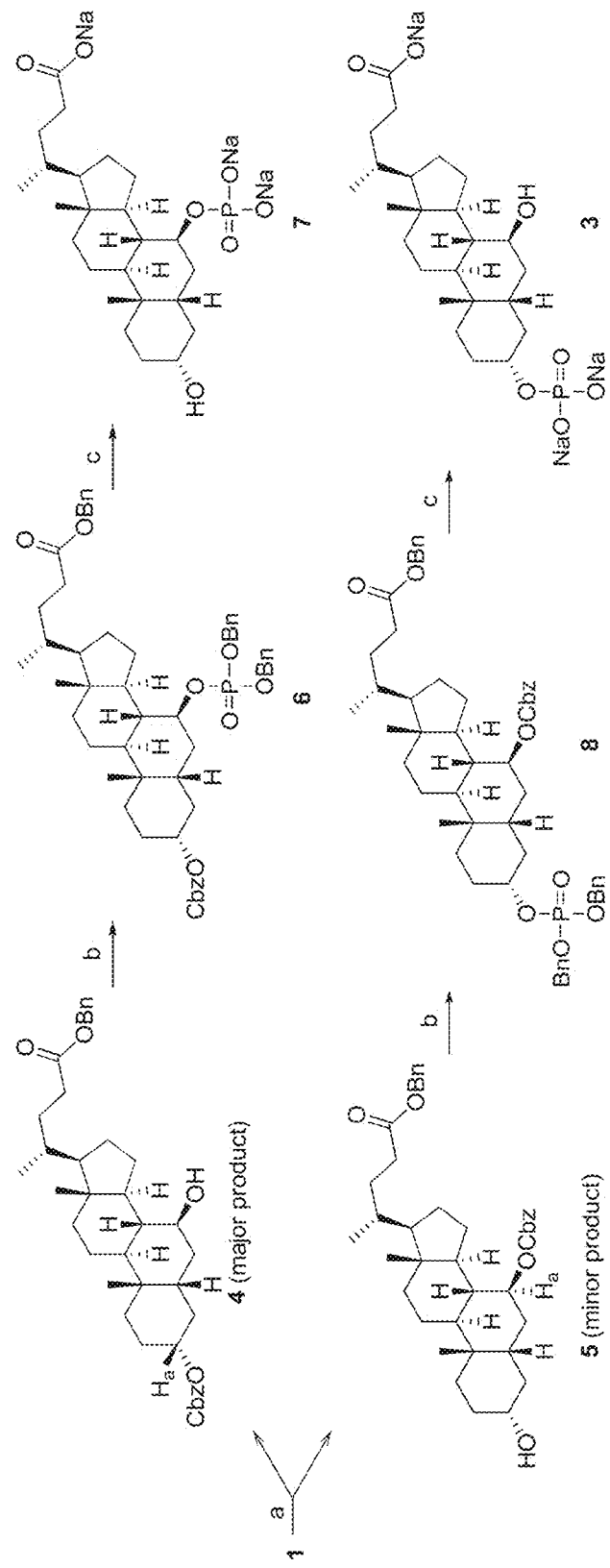
FIG. 2 illustrates synthesis of a 7-substituted phosphate prodrug (compound 7) and an alternate route to the 3-substituted phosphate prodrug (compound 3) of FIG. 1.

To obtain the 7-substituted phosphate ester prodrug of UDCA, benzyl ester 1 was treated with benzyl chloroformate and pyridine in dichloromethane as shown in FIG. 2. This led to a mixture of products, including 3-Cbz-protected alcohol (41%) (compound 4), 7-Cbz-protected alcohol (10%) (compound 5), and recovered starting material (41%). These products were readily separated by column chromatography, which allowed definitive confirmation of the regiochemistry of the prodrugs by $^1$H NMR analysis, as the signal of the proton next to the Cbz-protected alcohol ($H_a$ in FIG. 2) was a dddd in the major mono-substituted product (consistent with compound 4) and a ddd in the minor mono-substituted product (consistent with compound 5). Compound 4 was then converted into a 7-substituted phosphate ester prodrug (compound 7) using dibenzyl N,N-diethylphosphoramidite followed by oxidation with $H_2O_2$ and then Pd/C catalyzed debenzylation. Similar standard conditions converted compound 5 into the same 3-substituted phosphate ester prodrug (compound 3) that was obtained in FIG. 1. Both phosphate prodrugs (compound 3 and compound 7) were highly aqueously soluble, rapidly dissolving at all concentrations tested (up to 20 mg/mL), and were stable in solution for extended periods of time (>6 months) without any apparent decomposition. Reagents and conditions included: (a) benzyl chloroformate, pyridine, CH$_2$Cl$_2$; (b) i. dibenzyl N,N-diethylphosphoramidite, 1,2,4-triazole, NaHCO$_3$, Δ, ii. 30% H$_2$O$_2$, 0° C.; and (c) i. Pd/C, H$_2$, methanol, ii. Na$_2$CO$_3$.

In addition to compound 3 and compound 7, where the phosphate is directly linked to one of the alcohols in UDCA, synthesized 3- and 7-substituted oxymethylphosphate (OMP) UDCA prodrugs were also desired. OMP prodrugs (also referred to a phosphonooxymethyl or POM prodrugs) are typically bioactivated by alkaline phosphatase at a significantly faster rate than their directly linked phosphate ester analogs due to reduced steric hindrance, which would be preferred for rapid treatment of stroke or myocardial infarction. Upon bioactivation, OMP prodrugs release parent drug and formaldehyde in a two-step process.

Figure 3:
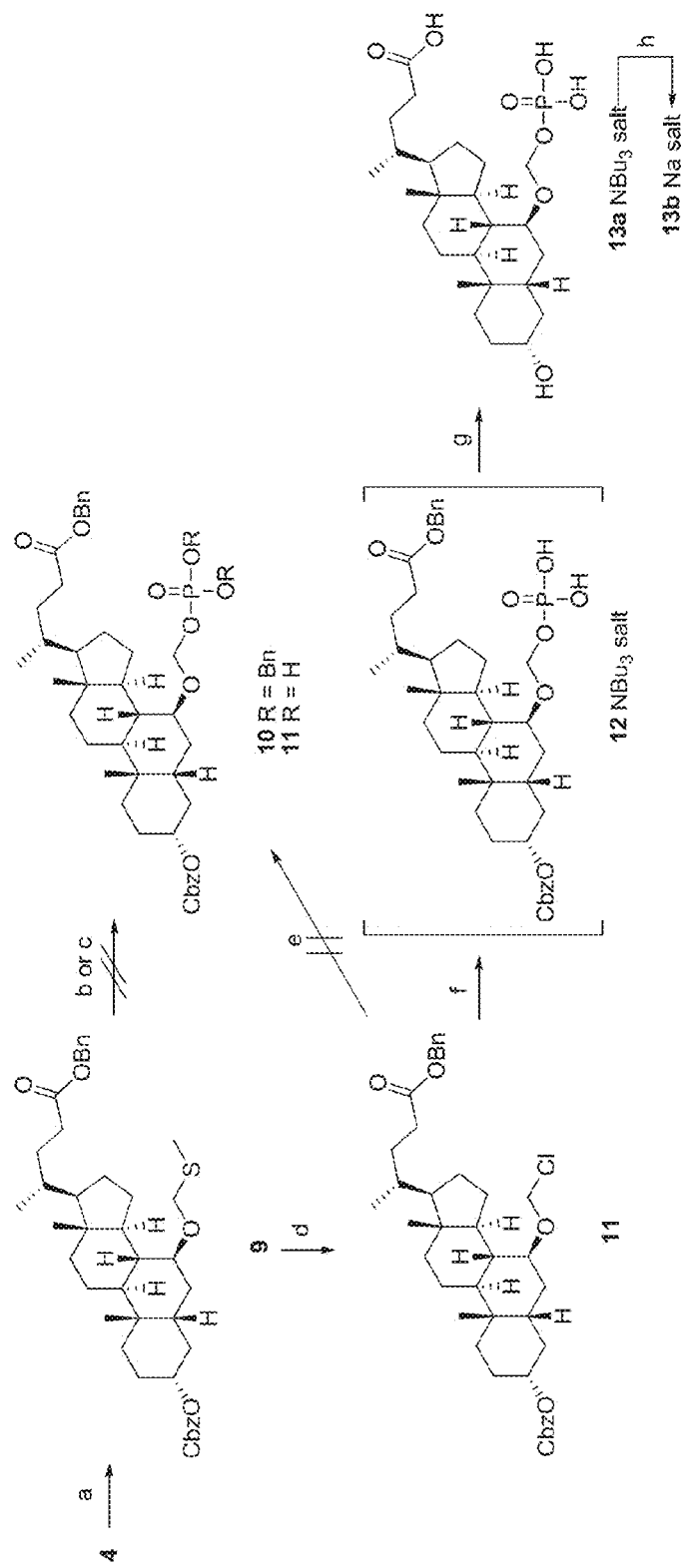
FIG. 3 illustrates synthesis of a 7-substituted oxymethylphosphate prodrug (compound 13).
Figure 4:
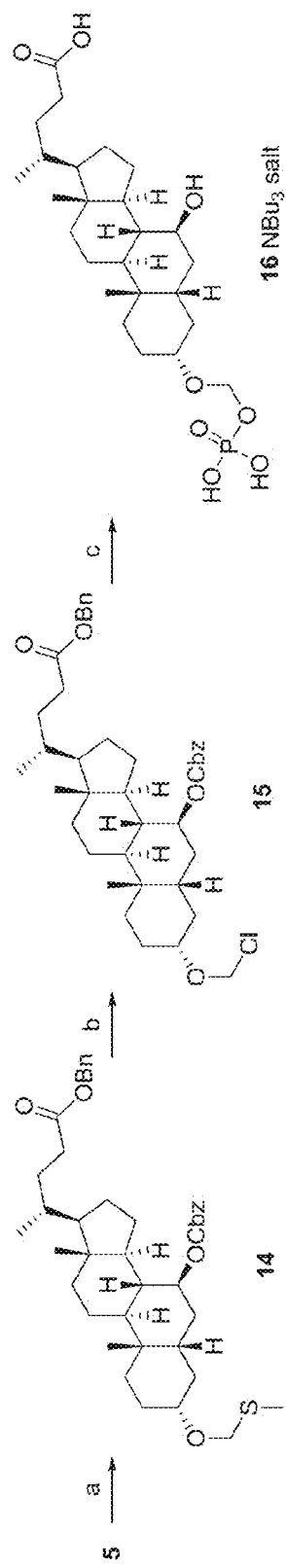
FIG. 4 illustrates synthesis of a 3-substituted oxymethylphosphate prodrug (compound 16).

The synthesis of the 3- and 7-substituted oxymethylphosphate (OMP) prodrugs of UDCA proved to be considerably more complicated than the synthesis of the directly linked phosphate prodrugs (compound 3 and compound 7). To synthesize the OMP prodrugs, a scheme that had previously been used to synthesize other OMP prodrugs, namely methylthiomethyl (MTM) ether formation followed by reaction with N-iodosuccinimide (NIS) and a phosphate, was used. The desired MTM ether intermediate (compound 9) was successfully synthesized by stirring compound 4 in DMSO, acetic anhydride, and acetic acid as shown in FIG. 3. A tri(n-butyl)amine salt of phosphate was successfully reacted with a chloroalkyl ether likely due to its improved solubility in organic solvents. Thus, stirring compound 11 with a tri(n-butyl)amine salt of phosphate in acetonitrile led to compound 12, which was then deprotected using hydrogen and Pd/C in methanol. The crude material was purified by C18 column to afford a 7-substituted OMP prodrug (compound 13a) as an NBu$_3$ salt. Reagents and conditions included: (a) DMSO, acetic anhydride, acetic acid; (b) dibenzyl phosphate, N-iodosuccinimide, molecular sieves; (c) H$_3$PO$_4$, N-iodosuccinimide, molecular sieves (d) SOCl$_2$, CH$_2$Cl$_2$, 100° C.; (e) dibenzyl phosphate, K$_2$CO$_3$, acetonitrile-d$_3$; (f) H$_3$PO$_4$, NBu$_3$, acetonitrile; (g) Pd/C, H$_2$, methanol; and (h) ion exchange using Na+-Dowex resin, MeOH/H$_2$O, Similarly, a 3-substituted OMP prodrug (compound 16) could be obtained from compound 5 using the same sequence of synthetic steps as shown in FIG. 4. Reagents and conditions include: (a) DMSO, acetic anhydride, acetic acid; (b) SOCl$_2$, CH$_2$Cl$_2$, 100° C.; and (c) i. H$_3$PO$_4$, NBu$_3$, acetonitrile, ii. Pd/C, H$_2$, methanol.

Due to the combination of chemical instability and the relatively difficult synthesis of the 3- and 7-substituted OMP prodrugs (compound 13a and compound 16), a prodrug where the OMP group is linked to the carboxylic acid of UDCA instead of one of its alcohols was prepared. Such a prodrug could potentially be bioactivated in vivo to the parent drug both by alkaline phosphatase and by esterases and has the additional advantage that the phosphate moiety is sterically unhindered (relative to the phosphate group in compound 3 or compound 7), which may increase the rate of enzymatic activation. Earlier work explored related phosphoryloxymethyloxy carbonyl prodrugs of alcohols, aliphatic amines and aromatic amines, but found their potential utility limited by chemical instability.

Figure 5:
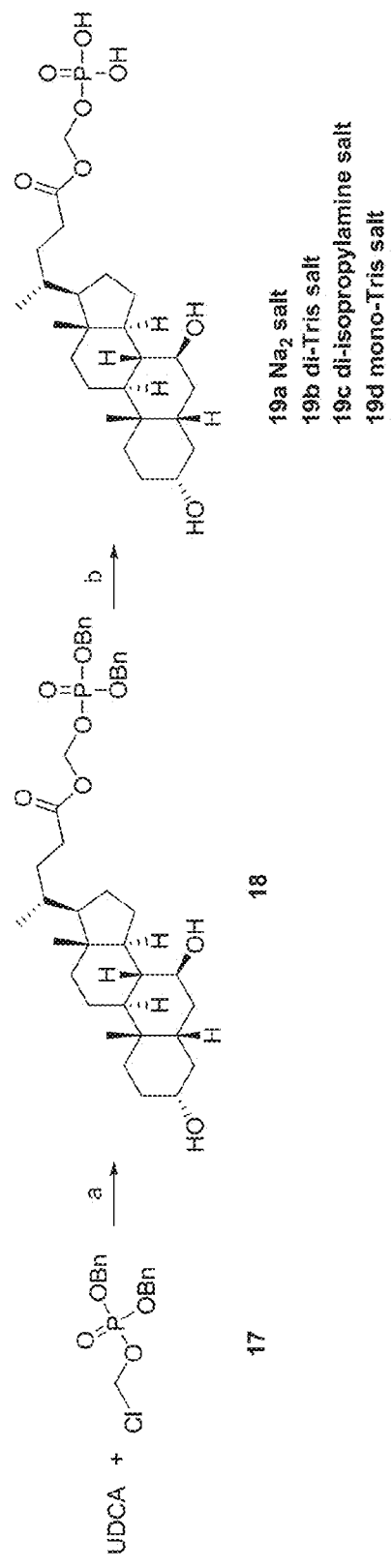
FIG. 5 illustrates synthesis of phosphoryloxymethyl carboxylate (POMC) prodrugs.

Synthesis of the phosphoryloxymethyl carboxylate (POMC) prodrug by reacting UDCA with K$_2$CO$_3$ and dibenzyl chloromethyl phosphate (compound 17) to afford the ester (compound 18) as shown in FIG. 5 was initiated. This reaction proceeded in higher yield (81% instead of 22%) and at much lower temperature (room temperature instead of 120° C.) when DMF was used as a solvent instead of acetonitrile. Using DMF instead of acetonitrile greatly minimized the formation of benzyl ester (compound 1) as a major side product. Next, after benzyl deprotection of compound 18 using hydrogen and Pd/C followed by treatment with two equivalents of tris(hydroxymethyl)aminomethane (Tris), the desired product was cleanly isolated as a diamine salt (compound 19b). Reagents and conditions included: (a) K$_2$CO$_3$, DMF; and (b) i. Pd/C, H$_2$, methanol, ii. Na$_2$CO$_3$, isopropylamine or Tris. The di-Tris salt of compound 19 was highly water-soluble, rapidly dissolving at all concentrations tested (up to 20 mg/mL), and stable for extended periods of time when stored in a freezer. However, it showed moderate chemical instability in solution at room temperature (only 36% remained after one week in D$_2$O solution, see FIG. 10). A diisopropylamine salt (compound 19c) showed similar chemical stability (34% remained after one week at room temperature in D$_2$O, see FIG. 10). However, formulations of compound 19 containing less than two equivalents of amine proved to be significantly more chemically stable in solution. Further synthesis led to the mono-Tris salt of our POMC prodrug (compound 19d), which was highly water soluble (>20 mg/mL), and decomposed relatively slowly in solution (88% remained after one week at room temperature in D$_2$O, see FIG. 10). The increased aqueous stability of the monoanionic prodrug relative to the dianionic prodrug is consistent with the hypothesis that hydrolysis occurs primarily via an intramolecular general base or intramolecular nucleophilic catalysis mechanism. This hypothesis is further supported by data showing that adding an additional equivalent of Tris to compound 19b has little effect on its stability in solution (see FIG. 10, entry 19e).

Figure 6:
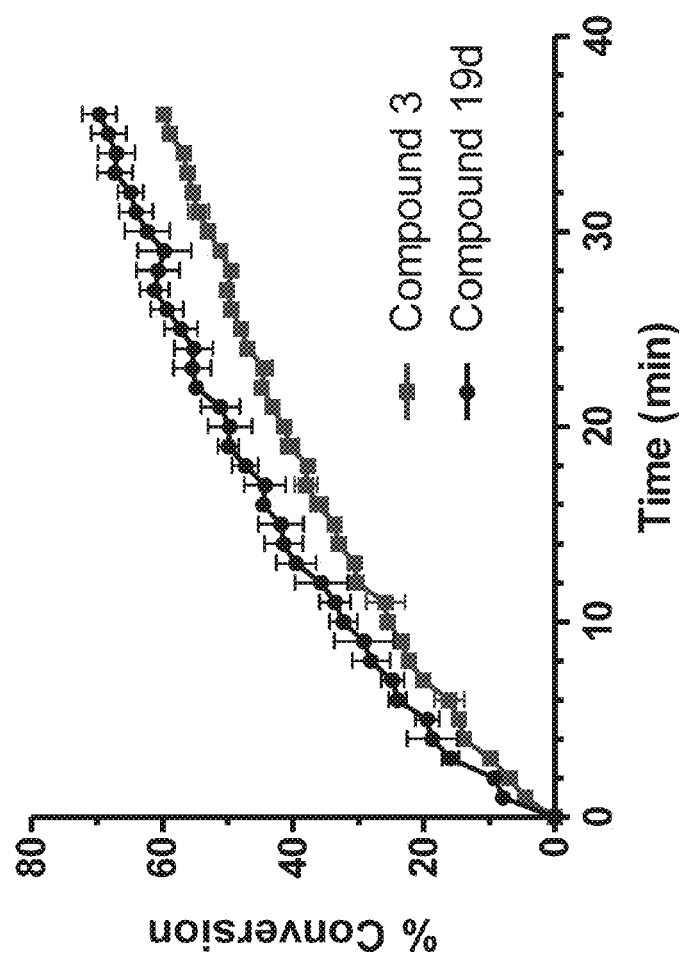
FIG. 6 is a graph of alkaline phosphatase catalyzed activation of compound 3 (shown in FIG. 1) and compound 19d (shown in FIG. 5).

To determine whether the POMC prodrug was indeed activated under in vitro conditions faster than a prodrug where the phosphate moiety is directly linked to an alcohol, a series of experiments were conducted monitoring the alkaline phosphatase catalyzed activation of the prodrugs compound 19d and compound 3 by inverse-gated decoupled $^{31}$P NMR. As shown in FIG. 6, UDCA was more rapidly released from prodrug compound 19d under in vitro conditions than prodrug compound 3. Each data point represents the mean of three separate experiments±standard error of the mean (SEM).

Figure 7:
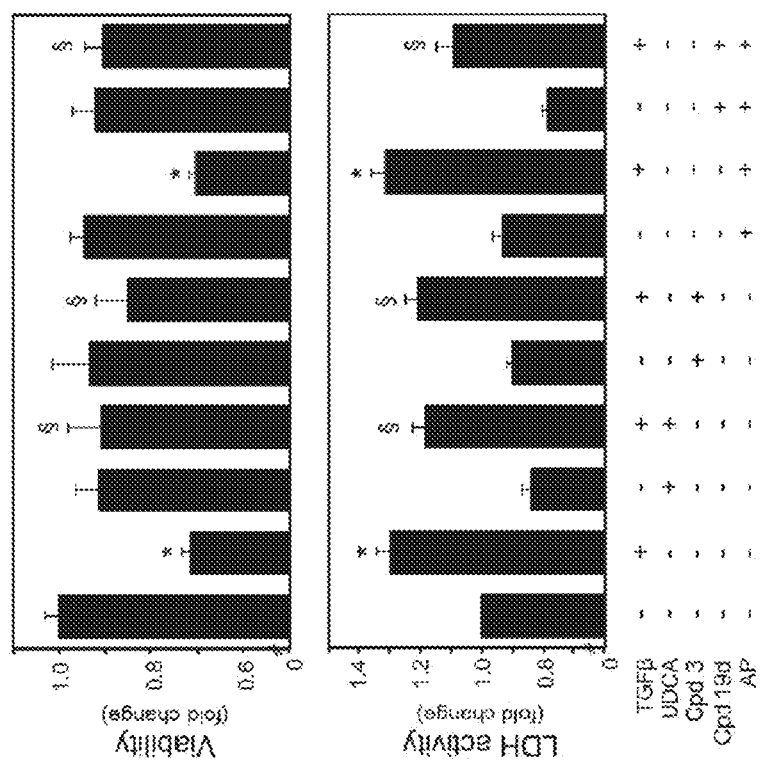
FIG. 7 illustrates graphs showing that compound 3 and compound 19d inhibit TGFβ-induced cytotoxicity in primary rat hepatocytes.

As noted previously, UDCA significantly inhibits caspase-3 activation and apoptosis induced by transforming growth factor β1 (TGFβ1) in primary rat hepatocytes. To compare the in vitro cytoprotective effects of the new prodrugs with UDCA, an alcohol-linked phosphate prodrug (the 3-substituted prodrug compound 3) and the POMC prodrug compound 19d were evaluated for their ability to modulate TGFβ1-induced cytotoxicity. Preliminary results demonstrated that the presence of alkaline phosphatase (AP) in the culture medium does not significantly change TGFβ1, UDCA or compound 3 cytotoxic and cytoprotective properties. However, compound 19d was cytoprotective only in the presence of AP. Therefore, AP was added to the culture medium whenever assessing the cytoprotective potential of compound 19d. The ability of compound 3 and compound 19d to inhibit TGFβ1-induced general cell death, as compared with UDCA were analyzed. The results showed that UDCA, compound 3 and alkaline phosphatase-activated compound 19d inhibited TGFβ1-induced loss of cellular viability by at least 50% (p<0.05) (see FIG. 7, upper panel). Results are expressed as means±SEM of at least three different experiments (*p<0.01 from respective control; §p<0.05 from respective TGFβ). In addition, TGFβ1 also induced a 30% increase in the amount of lactate dehydrogenase (LDH) released from cells, an indicator of cellular toxicity (p<0.01) (see FIG. 7, lower panel). Similarly as before, UDCA, compound 3 and compound 19d, inhibited TGFβ1-induced cytotoxicity by about 40, 30 and 60%, respectively (p<0.05).

Figure 8:
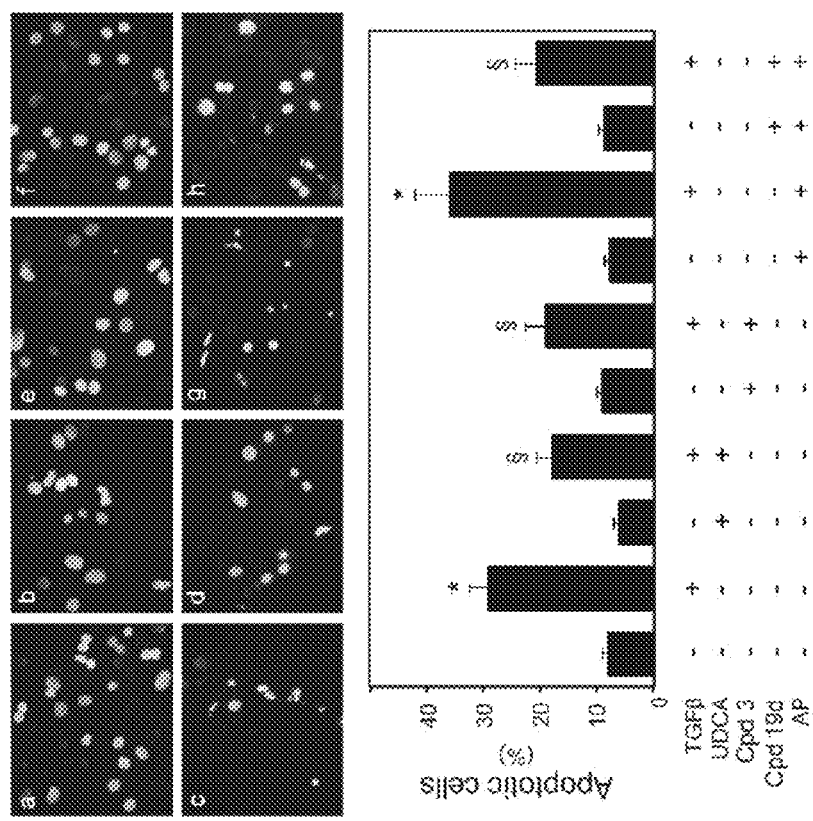
FIG. 8 illustrates photomicrographs and a graph showing that compound 3 and compound 19d inhibit TGFβ-induced nuclear fragmentation in primary rat hepatocytes.
Figure 9:
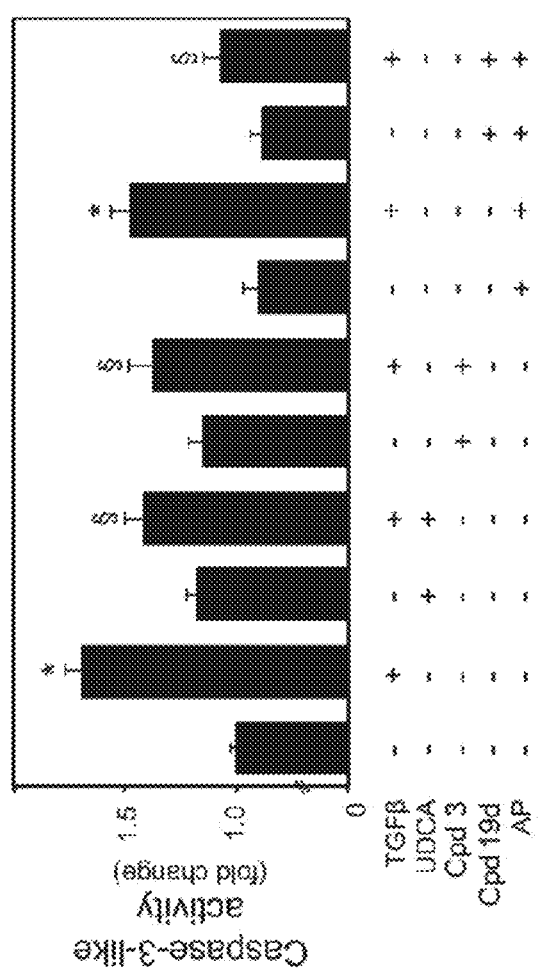
FIG. 9 illustrates a graph showing that TGFβ-induced caspase-3 activity is inhibited by compound 3 and compound 19d.

The effects of compound 3 and compound 19d on modulation of TGFβ1-induced apoptosis by changes in nuclear morphology (See FIG. 8) and by caspase activity (See FIG. 9) were then specifically evaluated. Results are expressed as means±SEM of at least three different experiments (*p<0.01 from respective control; §p<0.05 from respective TGFβ). Significant levels of apoptosis were found to have occurred in cultured primary rat hepatocytes after incubation with TGFβ1 (p<0.01), with a concomitant increase in caspase-3-like activity (p<0.01). Notably, UDCA, compound 3 and compound 19d protected against TGFβ1-induced nuclear fragmentation by 50-80% (p<0.05) and caspase-3-like activation by 40-70% (p<0.05). Altogether, these results show that much like UDCA, the newly synthesized UDCA prodrugs (compound 3 and compound 19d) display significant cytoprotective properties in vitro.

Five highly water-soluble prodrugs of the anti-apoptotic bile acid UDCA have been prepared from three distinct classes: directly linked phosphate esters, oxymethylphosphate (OMP) prodrugs and a phosphoryloxymethyl carboxylate (POMC) prodrug. As the OMP prodrugs of UDCA were both difficult to synthesize and chemically unstable, they were not tested in any biological assays. Compound 3, a directly linked phosphate ester, proved to have similar anti-apoptotic potency to UDCA as applied to in vitro assays, even without prior bioactivation by alkaline phosphatase. The POMC prodrug (compound 19), in contrast, was also highly active in these assays, but required activation by exogenous alkaline phosphatase to have an effect.

The POMC prodrug (compound 19) was bioactivated by alkaline phosphatase to UDCA faster than prodrug compound 3, in which the phosphate ester is directly linked to an alcohol. Pure mono and diamine salts of compound 19 could be readily obtained on a large scale (>5 g) in just two steps from the parent carboxylic acid (UDCA). Diamine salts of compound 19 were somewhat unstable in solution over long periods of time at ambient temperature, but the mono-Tris salt of compound 19 decomposed at a much slower rate and was stable for extended periods when stored cold.

Referring to FIG. 10, in one example, 4.0 mg of prodrug (compound 19b, compound 19c, or compound 19d) was dissolved in 1.0 mL $D_2O$. A sealed capillary tube containing phenylphosphonic acid dissolved in $D_2O$ was added as a standard. At time=0, a $^1H$ NMR spectrum was obtained and the proton signal at δ5.51 was integrated ($I_t$=0) relative to the aromatic signals from phenylphosphonic acid. After 7 days at room temperature, a new NMR spectrum was taken and the proton signal at δ5.51 was integrated again ($I_t$=7). The percent starting material remaining was $I_t$=7/$I_t$=0×100. Each experiment was repeated three times. Chemical stability results obtained either by measuring the disappearance of starting material relative to the internal standard by $^{31}P$ NMR or by using inverse-gated decoupled phosphorus NMR and integrating starting material and product were very similar to the numbers obtained using $^1H$ NMR. For compound 19e, 4.0 mg of compound 19b was dissolved in $D_2O$ and an additional equivalent of Tris added (the stoichiometry was confirmed by $^1H$ NMR) and the experiment conducted as above.

In another example, 4.0 mg of prodrug compound 19d was dissolved in 0.9 mL $H_2O$. To this solution was added 0.1 mL of Tris-buffered saline (BM-300 from Boston BioProducts, Ashland, Mass.), containing Tris (250 mM), KCl (27 mM), and NaCl (1.37 M). A sealed capillary tube containing phenylphosphonic acid dissolved in $D_2O$ was added as a standard. Chemical stability results were obtained by measuring the disappearance of starting material relative to the internal standard by $^{31}P$ NMR. The experiment was repeated three times. The standard deviation was ±3%.

In another example, alkaline phosphatase from bovine intestinal mucosa (P5521-2KU, Sigma-Aldrich, St. Louis, Mo.) was dissolved in 2.0 mL of a 0.100 M sodium glycine buffer containing 1.0 mM $ZnCl_2$ and 1.0 mM $MgCl_2$. This stock solution was stored at 4° C. between uses.

Compound 19d (10.0 mg, 0.016 mmol) or compound 3 (8.7 mg, 0.016 mmol) was dissolved in 0.6 mL of a 0.100 M Tris glycine buffer solution containing 1.0 mM $ZnCl_2$ and 1.0 mM $MgCl_2$. Neither compound showed decomposition by $^{31}P$ NMR when left in this buffer solution for 1 h. 50 μL of the previously prepared AP stock solution was further diluted by addition to 0.950 mL of a 0.100 M Tris glycine buffer containing 1.0 mM $ZnCl_2$ and 1.0 mM $MgCl_2$. 10.0 μL of this diluted AP solution was added to the prodrug solution by syringe. A series of 42 inverse-gated decoupled $^{31}P$ NMR's were taken (24 scans each, approximately one minute acquisition time). Conversion (%) was determined from the relative integration of the starting material and product peaks, NMR time stamps were used to determine time. Each experiment was repeated three times.

In another example, primary rat hepatocytes were isolated from male rats (100-150 g) by collagenase perfusion. Briefly, rats were anesthetized with phenobarbital sodium (100 mg/kg body weight) injected into the peritoneal cavity. After administration of heparin (200 units/kg body weight) in the tail vein, the animals' abdomen was opened and the portal vein exposed and cannulated. The liver was then perfused at 37° C. in situ with a calcium-free Hanks' Balanced Salt Solution (HBSS) for ~10 min, and then with 0.05% collagenase type IV in calcium-present HBSS for another 10 min. Hepatocyte suspensions were obtained by passing collagenase-digested livers through 125 μm gauze and washing cells in Complete William's E medium (Sigma-Aldrich) supplemented with 26 mM sodium bicarbonate, 23 mM HEPES (2-[4-(2-hydroxyethyl)piperazin-1-yl]ethanesulfonic acid), 0.01 units/mL insulin, 2 mM L-glutamine, 10 nM dexamethasone, 100 units/mL penicillin, and 10% heat-inactivated fetal bovine serum (Invitrogen, Carlsbad, Calif.). Viable primary rat hepatocytes were enriched by low-speed centrifugation at 200 g for 3 minutes. Cell viability was determined by trypan blue exclusion and was typically 80-85%. After isolation, hepatocytes were resuspended in Complete William's E medium and plated on Primaria™ tissue culture dishes (BD Biosciences, San Jose, Calif.) at 5×10$^4$ cells/cm$^2$. Cells were maintained at 37° C. in a humidified atmosphere of 5% $CO_2$ for 6 hours to allow attachment. Plates were then washed with medium to remove dead cells and incubated in Complete William's E medium supplemented with either 100 μM UDCA, compound 3, compound 19d or no addition (control), in the presence or absence of 3 U/ml of alkaline phosphatase (Invitrogen) for 12 hours. Cells were then exposed to 1 nmol/L recombinant human TGF-β1 (R&D Systems Inc., Minneapolis, Minn.) for 24 hours before processing for cell viability and apoptosis assays.

In another example, LDH, a stable cytosolic enzyme, is released to cell culture media following cell lysis, and can be used as a marker of cytotoxicity. Briefly, to assess LDH release, supernatants taken from a gentle centrifugation of cell culture media at 250 g, were combined in microplates with lactate (substrate), tetrazolium salt (coloring solution), and NAD (co-factor), previously mixed in equal proportions, following the manufacturer's instructions (Sigma-Aldrich). Multiwell plates were protected from light and incubated for 10 min at room temperature. Finally, absorbance was measured at 490 nm, with 690 nm as reference, using a Bio-Rad model 680-microplate reader (Bio-Rad Laboratories, Hercules, Calif.).

To assess cellular viability, the CellTiter-Fluor™ viability assay was used (Promega Corp., Madison, Wis.). Briefly, viable cells were measured using a fluorogenic, cell-permeant, peptide substrate (Gly-Phe-AFC), which is cleaved by the live-cell protease activity to generate a fluorescent signal proportional to the number of living cells. Cells were incubated with an equal volume of CellTiter-Fluor™ Reagent for 30 minutes at 37° C. and resulting fluorescence (380-400 $nm_{Ex}$/505 $nm_{Em}$) measured using a GloMax+ Multi Detection System (Promega Corp.).

In yet another example, general caspase-3/7 activity was evaluated using the Caspase-Glo® 3/7 Assay (Promega Corp.). Briefly, the assay provides a proluminescent caspase-3/7 DEVD-aminoluciferin substrate and a proprietary thermostable luciferase in a reagent optimized for caspase-3/7 activity, luciferase activity and cell lysis. Cells were incubated with an equal volume of Caspase-Glo® 3/7Reagent for 30 minutes at 37° C. and resulting luminescence measured using a GloMax+ Multi Detection System (Promega Corp.).

In addition, Hoechst labeling of cells was used to detect apoptotic nuclei by morphological analysis. Briefly, culture medium was gently removed to prevent detachment of cells. Attached primary rat hepatocytes were fixed with 4% paraformaldehyde in phosphate-buffered saline (PBS), pH 7.4, for 10 minutes at room temperature, washed with PBS, incubated with Hoechst dye 33258 (Sigma-Aldrich) at 5 µg/mL in PBS for 5 minutes, washed with PBS, and mounted using Fluoromount-G™ (SouthernBiotech). Fluorescence was visualized using an Axioskop fluorescence microscope (Carl Zeiss AG, Jena, Germany). Blue-fluorescent nuclei were scored blindly and categorized according to the condensation and staining characteristics of chromatin. Normal nuclei showed non-condensed chromatin disperse over the entire nucleus. Apoptotic nuclei were identified by condensed chromatin, contiguous to the nuclear membrane, as well as by nuclear fragmentation of condensed chromatin. Five random microscopic fields per sample containing approximately 150 nuclei were counted, and mean values expressed as the percentage of apoptotic nuclei.

Note that statistical analysis was performed using GraphPad InStat version 3.00 (GraphPad Software, San Diego, Calif.) for the analysis of variance and Bonferroni's multiple comparison tests. Values of $p<0.05$ were considered significant.

In another example, $^1$H NMR and $^{13}$C NMR Spectra were recorded on a Bruker 400 spectrometer. The $^1$H NMR data are reported as follows: chemical shift in parts per million downfield of tetramethylsilane (TMS), multiplicity (s=singlet, bs=broad singlet, d=doublet, t=triplet, q=quartet, quint=quintet and m=multiplet), coupling constant (Hz), and integrated value. Coupling constants listed as $J_{31P}$ disappeared when $^1$H NMR spectra were taken with $^{31}$P decoupling. The $^{13}$C NMR spectra were measured with complete proton decoupling. $^{31}$P NMR spectra taken for compound characterization were measured with complete proton decoupling and were referenced to 85% phosphoric acid, which was added to the NMR tube in a sealed capillary tube. LC/MS analysis was carried out using a BEH $C_{18}$ column (2.1 mm×50 mm, 5 um) on a Waters Acquity UPLC system with a Waters ZQ mass detector. Ursodeoxycholic acid was obtained from Sigma-Aldrich. Dibenzyl chloromethyl phosphate was synthesized by the method of Mäntylä, but is also commercially available from Sigma-Aldrich.

In another example, Ursodeoxycholic acid benzyl ester (compound 1) was created by the following procedure: a suspension of ursodeoxycholic acid (4.03 g, 10.3 mmol) and $K_2CO_3$ (4.88 g, 35.3 mmol) in acetonitrile (100 mL) was added to benzyl bromide (6.00 mL, 50.5 mmol). The reaction mixture was heated to 80° C. for 3 hours, filtered, and concentrated under reduced pressure. Purification by flash chromatography (30% to 100% ethyl acetate/hexanes) on silica gel furnished 4.72 g of white solid (95% yield). $^1$H NMR (400 MHz, $CD_3OD$): 7.39-7.28 (m, 5H), 5.13 and 5.10 (ABq, $J_{AB}$=12.3 Hz, 2H), 3.56-3.42 (m, 2H), 2.46-2.36 (m, 1H), 2.36-2.25 (m, 1H), 2.08-1.97 (m, 1H), 1.94-1.76 (m, 5H), 1.67-0.98 (m, 18H), 0.97 (s, 3H), 0.94 (d, J=6.4 Hz, 3H), 0.67 (s, 3H). $^{13}$C NMR ($CD_3OD$): 12.7, 18.9, 22.4, 23.9, 27.9, 29.6, 31.1, 32.2, 32.3, 35.2, 36.1, 36.6, 38.0, 38.6, 40.7, 41.5, 44.0, 44.5, 44.8, 56.5, 57.5, 67.2, 71.9, 72.1, 129.2, 129.3, 129.6, 137.7, 175.7.

In another example, 3-(Bis(benzyloxy)phosphoryloxy)-ursodeoxycholic acid benzyl ester (compound 2) was created by the following procedure detailed below. To a stirred suspension of ursodeoxycholic acid benzyl ester (compound 1) (1.497 g, 3.10 mmol), 1,2,4-triazole (450 mg, 6.52 mmol), and $NaHCO_3$ (1.906 g, 22.69 mmol) in 1,2-dichloroethane (30 mL) was added dibenzyl N,N-diethylphosphoramidite (1.00 mL, 3.15 mmol). The reaction mixture was heated overnight to 65° C. After cooling the mixture in an ice bath, tetrahydrofuran (THF) (12 mL) was added, followed by dropwise addition of 30% $H_2O_2$ (6 mL). After stirring for 5 minutes, saturated aqueous $Na_2S_2O_3$ (30 mL) was slowly added. The mixture was diluted with water (200 mL) and extracted with $CH_2Cl_2$ (2×200 mL). The combined organic layers were dried ($MgSO_4$), filtered, and concentrated under reduced pressure. Purification by flash chromatography (30% to 100% ethyl acetate/hexanes) on silica gel followed by a second flash chromatography (0 to 10% methanol/$CH_2Cl_2$) on silica gel furnished 1.1158 g product (48% yield) as a clear colorless oil. $^1$H NMR (400 MHz, $CDCl_3$): 7.43-7.27 (m, 15H), 5.12 and 5.09 (ABq, $J_{AB}$=12.4 Hz, 2H), 5.07-4.96 (m, 4H), 4.29-4.15 (m, 1H), 3.58-3.44 (m, 1H), 2.46-2.33 (m, 1H), 2.33-2.21 (m, 1H), 2.01-1.93 (m, 1H), 1.93-0.93 (m, 23H), 0.91 (s, 3H), 0.91 (d, J=6.1 Hz, 3H), 0.64 (s, 3H). $^{13}$C NMR ($CDCl_3$): 12.1, 18.4, 21.2, 23.2, 26.8, 28.2, 28.6, 31.0, 31.3, 33.9, 34.5, 34.8, 35.2, 36.5, 39.1, 40.1, 42.3, 43.66, 43.73, 54.9, 55.7, 66.1, 69.04, 69.07, 69.10, 69.12, 71.1, 78.6 (d, $J_{31P}$=6.0 Hz), 127.88, 127.90, 128.19, 128.25, 128.45, 128.54, 135.98, 136.05, 136.10, 174.0. HRMS calculated for $C_{45}H_{59}O_7P+H^+$, 743.4077. observed, 743.4092.

In another example, 3-(Phosphonatooxy)-ursodeoxycholic acid sodium salt (compound 3) was created by the following procedure. To a solution of compound 2 (FIG. 1) (2.22 g, 2.99 mmol) in methanol (100 mL) was added 10% Pd/C (291 mg). The reaction mixture was stirred under a balloon filled with hydrogen for 2 hours and filtered through celite. $Na_2CO_3$ (476 mg, 4.49 mmol) dissolved in water (25 mL) was added and the solution concentrated under reduced pressure until most of the methanol was removed. The remaining solution was lyophilized to afford 1.627 g of product as a white solid. $^1$H NMR (400 MHz, $D_2O$): 4.04-3.91 (m, 1H), 3.72-3.62 (m, 1H), 2.29-2.17 (m, 1H), 2.17-2.06 (m, 1H), 2.07-1.97 (m, 1H), 1.95-1.00 (m, 23H), 0.96 (s, 3H), 0.95 (d, J=6.0 Hz, 3H), 0.70 (s, 3H). $^{13}$C NMR ($D_2O$): 12.1, 18.6, 21.5, 23.3, 27.2, 28.8, 29.0, 33.1, 34.1, 35.2, 35.3, 35.7, 35.8, 37.1, 39.6, 40.4, 42.9, 43.5, 44.0, 55.1, 55.7, 71.9, 75.9 (d, $J_{31P}$=5.0 Hz), 185.5. $^{31}$P NMR (D$_2$O): 2.51. HRMS calculated for $C_{24}H_{41}O_7P+H^+$, 473.2668. observed, 473.2670.

In another example, 3-(Benzyloxycarbonyloxy)-ursodeoxycholic acid benzyl ester (compound 4) and 7-(benzyloxycarbonyloxy)-ursodeoxycholic acid benzyl ester (compound 5) were created with the following procedure. To a stirred solution of ursodeoxycholic acid benzyl ester (compound 1) (1.465 g, 3.04 mmol) in dry CH$_2$Cl$_2$ (50 mL) was added pyridine (0.600 mL, 7.42 mmol) followed by slow addition of benzyl chloroformate (1.00 mL, 7.03 mmol). After stirring for one hour, additional pyridine (0.300 mL, 3.71 mmol) and benzyl chloroformate (0.600 mL, 4.22 mmol) were added. After an addition 30 minutes, the reaction mixture was extracted with 1M HCl (50 mL). The organic layer was dried (Na$_2$SO$_4$), filtered, and concentrated under reduced pressure. Purification by flash chromatography (10% to 100% ethyl acetate/hexanes) on silica gel furnished first compound 4 (0.7769 g, 41% yield) as a slightly yellow foam, followed by compound 5 (181 mg, 10% yield) as a slightly yellow foam, which was then followed by recovered starting material ursodeoxycholic acid benzyl ester (compound 1) (603.2 mg, 41%) as a white solid.

3-(Benzyloxycarbonyloxy)-ursodeoxycholic acid benzyl ester (compound 4): $^1$H NMR (400 MHz, CDCl$_3$): 7.39-7.30 (m, 10H), 5.14 (s, 2H), 5.12 and 5.09 (ABq, $J_{AB}$=12.3 Hz, 2H), 4.56 (dddd, J=5, 5, 11, 11 Hz, 1H), 3.60-3.50 (m, 1H), 2.45-2.34 (m, 1H), 2.33-2.22 (m, 1H), 2.02-1.94 (m, 1H), 1.94-0.98 (m, 23H), 0.95 (s, 3H), 0.91 (d, J=6.2 Hz, 3H), 0.65 (s, 3H). $^{13}$C NMR (CDCl$_3$): 12.1, 18.3, 21.2, 23.3, 26.4, 26.9, 28.6, 31.0, 31.3, 33.0, 34.1, 34.5, 35.2, 36.6, 39.1, 40.1, 42.2, 43.7, 43.8, 54.9, 55.7, 66.1, 69.3, 71.2, 77.9, 128.18, 128.24, 128.28, 128.46, 128.54, 128.57, 135.4, 136.1, 154.5, 174.0.

7-(Benzyloxycarbonyloxy)-ursodeoxycholic acid benzyl ester (compound 5): $^1$H NMR (400 MHz, CDCl$_3$): 7.39-7.30 (m, 10H), 5.16 and 5.12 (ABq, $J_{AB}$=12.2 Hz, 2H), 5.12 and 5.10 (ABq, $J_{AB}$=12.3 Hz, 2H), 4.64 (ddd, J=5, 11, 11 Hz, 1H), 3.63-3.52 (m, 1H), 2.44-2.34 (m, 1H), 2.32-2.22 (m, 1H), 2.01-1.93 (m, 1H), 1.91-0.96 (m, 23H), 0.94 (s, 3H), 0.90 (d, J=6.3 Hz, 3H), 0.62 (s, 3H). $^{13}$C NMR (CDCl$_3$): 12.0, 18.3, 21.2, 23.2, 25.6, 28.6, 30.2, 31.0, 31.3, 33.0, 33.9, 34.7, 35.2, 37.1, 39.4, 39.9, 40.0, 42.2, 43.6, 55.0, 55.2, 66.1, 69.3, 71.3, 78.5, 128.11, 128.19, 128.24, 128.39, 128.54, 128.56, 135.6, 136.1, 154.6, 174.0

In another example, 3-(Benzyloxycarbonyloxy)-7-(bis(benzyloxy)phosphoryloxy)-ursodeoxycholic acid benzyl ester (compound 6) was created with the following procedure. To a stirred suspension of compound 4 (374 mg, 0.61 mmol), 1,2,4-triazole (89.8 mg, 1.30 mmol), and NaHCO$_3$ (263 mg, 3.13 mmol) in CH$_2$Cl$_2$ was added dibenzyl N,N-diethylphosphoramidite (0.900 mL, 3.00 mmol). The reaction mixture was heated overnight to 40° C. After cooling the mixture in an ice bath, THF (5 mL) was added, followed by dropwise addition of 30% H$_2$O$_2$ (3 mL). After stirring for 5 minutes, saturated aqueous Na$_2$S$_2$O$_3$ (20 mL) was slowly added. The mixture was diluted with CH$_2$Cl$_2$ and extracted with water (100 mL). The organic layer was dried (Na$_2$SO$_4$), filtered, and concentrated under reduced pressure. Purification by flash chromatography (30% ethyl acetate/hexanes) on silica gel furnished 350.1 mg product (66% yield) as a slightly yellow oil. $^1$H NMR (400 MHz, CDCl$_3$): 7.43-7.27 (m, 20H), 5.16 and 5.15 (ABq, $J_{AB}$=12.4 Hz, 2H), 5.12 and 5.10 (ABq, $J_{AB}$=12.4 Hz, 2H), 5.05-4.91 (m, 4H), 4.51 (dddd, J=5, 5, 10, 10 Hz, 1H), 4.30-4.17 (m, 1H), 2.45-2.34 (m, 1H), 2.32-2.21 (m, 1H), 1.99-0.99 (m, 24H), 0.93 (s, 3H), 0.90 (d, J=6.1 Hz, 3H), 0.61 (s, 3H). $^{13}$C NMR (CDCl$_3$): 12.1, 18.4, 21.2, 23.2, 26.2, 28.4, 31.0, 31.3, 32.7, 33.8, 34.3, 34.4, 35.2, 39.2, 39.8, 41.8, 41.9, 42.0, 43.7, 54.9, 55.0, 66.1, 68.86, 68.92, 69.00, 69.05, 69.4, 77.5, 79.69, 79.75, 127.86, 127.90, 128.17, 128.22, 128.27, 128.40, 128.47, 128.54, 128.59, 135.4, 136.09, 136.11, 136.15, 136.18, 154.5, 174.0. LC/MS calculated for $C_{53}H_{65}O_9P+H^+$, 877.4. observed, 877.7.

In another example, 7-(Phosphonatooxy)-ursodeoxycholic acid sodium salt (compound 7) was created with the following procedure. To a suspension of compound 6 (1.1984 g, 1.37 mmol) in methanol (200 mL) was added 10% Pd/C (322 mg). The reaction mixture was stirred under a balloon filled with hydrogen for 2 hours and filtered through celite. Na$_2$CO$_3$ (216.2 mg, 2.04 mmol) dissolved in water (25 mL) was added and the solution concentrated under reduced pressure until most of the methanol was removed. The remaining solution was lyophilized to afford 762.7 mg of product as a white solid. $^1$H NMR (400 MHz, D$_2$O): 4.13-3.99 (m, 1H), 3.69-3.55 (m, 1H), 2.30-2.17 (m, 1H), 2.17-2.07 (m, 1H), 2.07-1.92 (m, 3H), 1.92-0.99 (m, 21H), 0.97 (s, 3H), 0.95 (d, J=6.5 Hz, 3H), 0.69 (s, 3H). $^{13}$C NMR (D$_2$O): 12.1, 18.6, 21.5, 23.4, 27.0, 28.8, 29.6, 33.1, 34.1, 35.0, 35.2, 35.4, 35.9, 36.4, 39.5, 40.2, 42.6, 42.7, 44.0, 55.1, 55.3, 72.0, 76.4 (d, $J_{31P}$=5.9 Hz), 185.6. $^{31}$P NMR (D$_2$O): 0.93. LC/MS calculated for $(C_{24}H_{41}O_7P-H)^-$, 471.3. observed, 471.4.

In another example, 3-(Benzyloxycarbonyloxy)-7-(methylthiomethoxy)-ursodeoxycholic acid benzyl ester (compound 9) was created with the following procedure. To a solution of compound 4 (2.71 g, 4.39 mmol) in dimethyl sulfoxide (DMSO) (34 mL) was added acetic anhydride (21 mL) followed by acetic acid (34 mL). After stirring at room temperature for 24 hours, the reaction mixture was diluted with water (500 mL) and neutralized with NaHCO$_3$. The mixture was extracted with ethyl acetate (500 mL). The organic layer was then further extracted with water (5×500 mL), dried (Na$_2$SO$_4$), filtered, and concentrated under reduced pressure. Purification by flash chromatography (5% to 30% ethyl acetate/hexanes) on silica gel furnished 1.3966 g of product (47% yield) as a slightly yellow oil. $^1$H NMR (400 MHz, CDCl$_3$): 7.40-7.28 (m, 10H), 5.14 (s, 2H), 5.12 and 5.09 (ABq, $J_{AB}$=12.4 Hz, 2H), 4.61-4.50 (m, 1H), 4.59 and 4.52 (ABq, $J_{AB}$=11.2 Hz, 2H), 3.33 (ddd, J=5, 11, 11 Hz, 1H), 2.45-2.35 (m, 1H), 2.32-2.22 (m, 1H), 2.17 (s, 3H), 2.00-1.93 (m, 1H), 1.92-0.97 (m, 23H), 0.95 (s, 3H), 0.90 (d, J=6.2 Hz, 3H), 0.63 (s, 3H). $^{13}$C NMR (CDCl$_3$): 12.2, 15.3, 18.4, 21.3, 23.3, 26.3, 26.6, 28.5, 31.0, 31.3, 32.5, 33.0, 34.1, 34.5, 35.2, 39.4, 40.1, 41.5, 42.0, 43.8, 55.0, 55.8, 66.1, 69.4, 73.0, 77.9, 78.1, 128.16, 128.23, 128.28, 128.46, 128.54, 128.57 135.4, 136.2, 154.6, 174.1.

In another example, 3-(Benzyloxycarbonyloxy)-7-(chloromethoxy)-ursodeoxycholic acid benzyl ester (compound 11) was created with the following procedure. To a solution of compound 9 (847 mg, 1.25 mmol) in dry CH$_2$Cl$_2$ (20 mL) was added 2M SOCl$_2$ in CH$_2$Cl$_2$ (1.9 mL, 3.8 mmol). The reaction mixture was heated in a microwave to 100° C. for 30 minutes and then concentrated under reduced pressure. A $^1$H NMR spectrum of the crude material in CDCl$_3$ showed a new set of doublets δ5.56 and 5.47 (J=5.4 Hz, 1H each) and the disappearance of the AB pattern at δ4.59 and 4.52 as well as the SMe peak which had been at δ2.17 in the $^1$H NMR spectrum of compound 9. The crude material was used without further purification in the next reaction.

In another example, 7-(Phosphonooxymethoxy)-ursodeoxycholic acid tributylamine salt (compound 13a) was created with the following procedure. To a suspension of H$_3$PO$_4$ (586 mg, 5.98 mmol) and 4 Å molecular sieves (2.023 g) in acetonitrile (40 mL) was added Bu$_3$N (5.4 mL, 22.7 mmol). The mixture was stirred overnight and then added to a flask containing crude compound 11. After stirring for 24 hours, the mixture was filtered through celite and concentrated under reduced pressure. The residue was dissolved in methanol (50 mL) and concentrated under reduced pressure again. Next, the residue was dissolved in methanol (50 mL), 10% Pd/C (2.369 g) added, and the reaction mixture stirred under a balloon filled with hydrogen for 2 hours and then filtered through celite. Additional 10% Pd/C (2.14 g) was added and the reaction mixture stirred under a balloon filled with hydrogen for 72 hours. The reaction mixture was filtered through celite and concentrated under reduced pressure. The resulting residue purified by chromatography (5% acetonitrile/water to 100% acetonitrile, C$_{18}$ column) to yield 116.7 mg white solid after lyophilization. There are approximately 1.4 equivalents of NBu$_3$ present for every equivalent of bile acid based on $^1$H NMR analysis (comparison of the integration of the methyl peak at δ0.70 to the multiplet at δ3.12-3.02). $^1$H NMR (400 MHz, CD$_3$OD): 5.18 (dd, J=6 Hz, J$_{31P}$=6 Hz, 1H), 4.99 (dd, J=6 Hz, J$_{31P}$=8 Hz, 1H), 3.66-3.55 (m, 1H), 3.53-3.42 (m, 1H), 3.13-3.02 (m, 8.2H), 2.35-2.24 (m, 1H), 2.20-2.10 (m, 1H), 2.08-1.98 (m, 1H), 1.94-0.90 (m, 57H), 0.70 (s, 3H). LC/MS calculated for (C$_{25}$H$_{43}$O$_8$P—H)$^-$, 501.3. observed, 501.3.

In another example, 7-(Phosphonooxymethoxy)-ursodeoxycholic acid sodium salt (compound 13b) was created with the following procedure. A 1 cm wide column was filled with 12 cm of DOWEX 50W2 (50-100 mesh, strongly acidic) ion exchange resin. The column was prepared by sequentially washing with 1:1 methanol/water, 1M aqueous NaHCO$_3$, water, and then finally 1:1 methanol/water. Compound 13a (115 mg) was dissolved in 1:1 methanol/water and loaded onto the column, which was eluted with 1:1 methanol/water. The product containing fractions were lyophilized to furnish the product as a white solid (76.4 mg). $^1$H NMR (400 MHz, D$_2$O): 5.18 (dd, J=5.7 Hz, J$_{31P}$=6.8 Hz, 1H), 4.99 (dd, J=5.7 Hz, J$_{31P}$=9.4 Hz, 1H), 3.74-3.56 (m, 2H), 2.40-2.28 (m, 1H), 2.27-2.14 (m, 1H), 2.08 (m, 24H), 1.00-0.92 (m, 6H), 0.70 (s, 3H).

In another example, 3-(Methylthiomethoxy)-7-(benzyloxycarbonyloxy)-ursodeoxycholic acid benzyl ester (compound 14) was created with the following procedure. To a solution of compound 5 (1.113 g, 1.80 mmol) in DMSO (17 mL) was added acetic anhydride (10.5 mL) followed by acetic acid (17 mL). After stirring at room temperature for 24 hours, the reaction mixture was diluted with water (500 mL) and neutralized with NaHCO$_3$. The mixture was extracted with ethyl acetate (500 mL). The organic layer was then further extracted with water (5×500 mL), dried (Na$_2$SO$_4$), filtered, and concentrated under reduced pressure. Purification by flash chromatography (5% to 50% ethyl acetate/hexanes) on silica gel furnished 364 mg of product (30% yield) as a slightly yellow oil. $^1$H NMR (400 MHz, CDCl$_3$): 7.41-7.28 (m, 10H), 5.16 and 5.12 (ABq, J$_{AB}$=12.0 Hz, 2H), 5.12 and 5.10 (ABq, J$_{AB}$=12.4 Hz, 2H), 4.67-4.58 (m, 1H), 4.65 (s, 2H), 3.57 (dddd, J=5, 5, 10, 10 Hz, 1H), 2.44-2.34 (m, 1H), 2.31-2.22 (m, 1H), 2.15 (s, 3H), 2.00-1.93 (m, 1H), 1.92-0.95 (m, 23H), 0.94 (s, 3H), 0.89 (d, J=6.3 Hz, 3H), 0.62 (s, 3H). $^{13}$C NMR (CDCl$_3$): 12.2, 13.7, 18.3, 21.2, 23.2, 25.6, 26.9, 28.4, 31.0, 31.3, 33.1, 33.4, 34.2, 34.7, 35.2, 39.2, 39.9, 40.0, 42.2, 43.6, 55.0, 55.2, 66.1, 69.3, 72.0, 75.2, 78.5, 128.10, 128.18, 128.24, 128.39, 128.64, 135.6, 136.1, 154.6, 174.0.

In another example, 3-(Chloromethoxy)-7-(benzyloxycarbonyloxy)-ursodeoxycholic acid benzyl ester (compound 15) was created with the following procedure. To a solution of compound 14 (360 mg, 0.53 mmol) in dry CH$_2$Cl$_2$ (20 mL) was added 2M SOCl$_2$ in CH$_2$Cl$_2$ (0.8 mL, 1.6 mmol). The reaction mixture was heated in a microwave to 100° C. for 30 minutes and then concentrated under reduced pressure. A $^1$H NMR spectrum of the crude material in CDCl$_3$ showed a new AB pattern at δ5.55 and 5.54 (J=5.4 Hz, 2H total) and the disappearance of the singlet at δ4.65 as well as the SMe peak which had been at δ2.15 in the $^1$H NMR spectrum of compound 14. The crude material was used without further purification in the next reaction.

In another example, 3-(Phosphonooxymethoxy)-ursodeoxycholic acid tributylamine salt (compound 16) was created with the following procedure. To a suspension of H$_3$PO$_4$ (248 mg, 2.53 mmol) and 4 Å molecular sieves (0.760 g) in acetonitrile (15 mL) was added Bu$_3$N (2.3 mL, 9.68 mmol). The mixture was stirred overnight and then added to a flask containing the crude product of the previous reaction (compound 14). After stirring for 72 hours, the mixture was filtered and concentrated under reduced pressure. The residue was dissolved in methanol (25 mL) and concentrated under reduced pressure again. Next, the residue was dissolved in methanol (40 mL), 10% Pd/C (656 mg) added, and the reaction mixture stirred under a balloon filled with hydrogen for 2 hours and then filtered through celite. A crude NMR of an aliquot showed no reaction. Additional 10% Pd/C (744 mg) was added and the reaction mixture stirred under a balloon filled with hydrogen for 2 hours and filtered through celite. A crude NMR of an aliquot again showed no reaction. Additional 10% Pd/C (1901 mg) was added and the reaction mixture stirred under a balloon filled with hydrogen overnight, filtered through celite and concentrated under reduced pressure. The resulting residue purified by chromatography (5% acetonitrile/water to 100% acetonitrile, C$_{18}$ column) to yield 80.7 mg white solid after lyophilization. There are approximately 1.7 equivalents of NBu$_3$ present for every equivalent of bile acid based on $^1$H NMR analysis (comparison of the integration of the methyl peak at δ0.71 to the multiplet at δ3.12-3.02). $^1$H NMR (400 MHz, CD$_3$OD): 5.08 (d, J$_{31P}$=8.4 Hz, 2H), 3.75-3.63 (m, 1H), 3.54-3.43 (m, 1H), 3.12-2.98 (m, 10H), 2.34-2.23 (m, 1H), 2.19-2.09 (m, 1H), 2.08-20 (m, 1H), 1.94-0.90 (m, 68H), 0.71 (s, 3H). LC/MS calculated for (C$_{25}$H$_{43}$O$_8$P—H)$^-$, 501.3. observed, 501.3.

In another example, Ursodeoxycholic acid (bis(benzyloxy)phosphoryloxy)methyl ester (compound 18) was created with the following procedure. To a suspension of ursodeoxycholic acid (1.46 g, 3.72 mmol) and K$_2$CO$_3$ (984 mg, 7.12 mmol) in dimethylformamide (DMF) (10 mL) was added dibenzyl chloromethyl phosphate (1.23 g, 3.76 mmol). The mixture was stirred overnight, diluted with water (250 mL), and extracted with ethyl acetate (3×250 mL) and CH$_2$Cl$_2$ (1×250 mL). The combined organic layers were dried (MgSO$_4$), filtered, and concentrated under reduced pressure. Purification by flash chromatography (40% to 100% ethyl acetate/hexanes) on silica gel furnished 2.05 g of clear, colorless foamy oil (81% yield). $^1$H NMR (400 MHz, CD$_3$OD): 7.42-7.38 (m, 10H), 5.64 (d, J$_{31P}$=13.8

Hz, 2H), 5.10 (d, $J_{31P}$=8.3 Hz, 4H), 3.58-3.44 (m, 2H), 2.41-2.31 (m, 1H), 2.29-2.18 (m, 1H), 2.08-1.98 (m, 1H), 1.96-1.72 (m, 5H), 1.70-1.00 (m, 18H), 0.99 (s, 3H), 0.93 (d, J=6.5 Hz, 3H), 0.71 (s, 3H). $^{13}$C NMR (CD$_3$OD): 12.7, 18.9, 22.4, 23.9, 27.9, 29.6, 31.1, 31.6, 31.8, 35.2, 36.1, 36.5, 38.0, 38.6, 40.7, 41.5, 44.0, 44.5, 44.8, 56.4, 57.5, 71.1 (d, $J_{31P}$=5.9 Hz), 71.9, 72.1, 83.9 (d, $J_{31P}$=5.7 Hz), 129.2, 129.7, 129.8, 136.9, 137.0, 173.8. $^{31}$P NMR (CD3OD): −1.59. HRMS calculated for $C_{39}H_{55}O_8P+H^+$, 683.3713. observed, 683.3735.

In another example, the synthesis of salts of ursodeoxycholic acid phosphonooxymethoxy ester (compound 19) was created with the following procedure. To a solution of compound 18 in methanol was added 10% Pd/C. The reaction mixture was stirred under a balloon filled with hydrogen for 45 minutes and filtered through celite. Amine was added (1 or 2 equivalents) and the solution concentrated under reduced pressure. Data for mono-Tris Salt (19d) $^1$H NMR (400 MHz, D$_2$O): 5.51 (d, $J_{31P}$=12.8 Hz, 2H), 3.74 (s, 6H), 3.60-3.54 (m, 2H), 2.58-2.46 (m, 1H), 2.44-2.32 (m, 1H), 2.09-1.98 (m, 1H), 1.96-1.74 (m, 5H), 1.72-1.02 (m, 18H), 1.01-0.95 (m, 6H), 0.72 (s, 3H). $^{13}$C NMR (D$_2$O): 12.6, 19.0, 22.0, 23.9, 27.2, 29.0, 30.2, 31.1, 31.4, 34.4, 35.4, 35.7, 36.6, 37.3, 39.9, 40.8, 42.8, 43.7, 44.1, 55.3, 56.1, 60.0, 62.1, 71.6, 71.7, 83.6, 176.4. $^{31}$P NMR (D$_2$O): −0.30. HRMS calculated for $(C_{25}H_{43}O_8P-H)^-$, 501.2617. observed, 501.2585.

The above Detailed Description includes references to the accompanying drawings, which form a part of the Detailed Description. The drawings and descriptions show, by way of illustration, specific embodiments in which the present disclosed prodrugs and related methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "including" and "comprising" are open-ended, that is, an assembly, system, or method that includes elements in addition to those listed after such a term in a claim are still deemed to fall within the scope of that claim. Moreover, in the following claims, the terms "first," "second," and "third," etc., if used, are merely used as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

It will be understood from the Detailed Description, below, that the present subject matter can be implemented in a multitude of different sizes, shapes, fit and function embodiments. While described in the context of a synthesized, water-soluble prodrug compound, it will be apparent to those skilled in the art that the present disclosure could be used in a number of varying applications.

What is claimed is:

1. A compound having the general formula

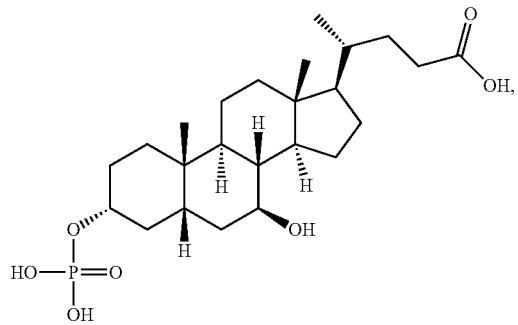

or a pharmaceutically acceptable salt thereof.

2. A compound having the general formula

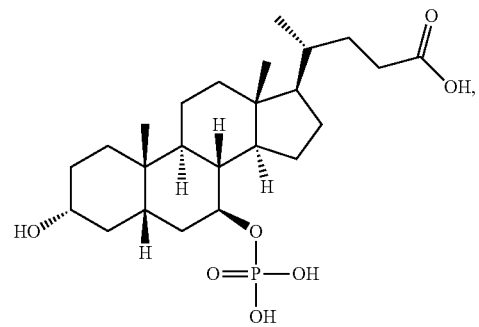

or a pharmaceutically acceptable salt thereof.

3. A compound having the general formula

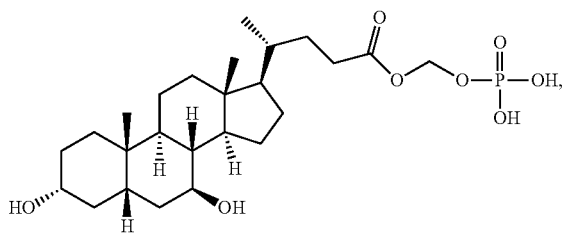

or a pharmaceutically acceptable salt thereof.

4. The disodium salt of the molecule having the general formula

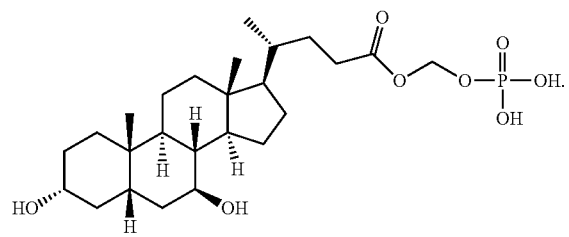
5. The tris(hydroxymethyl)aminomethane salt of the molecule having the general formula
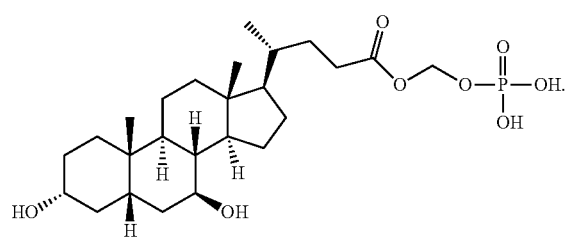
7. The diisopropylamine salt of the molecule having the general formula
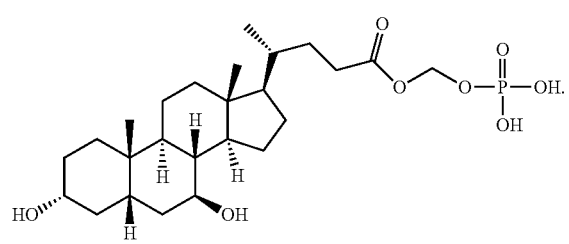
6. The di-tris(hydroxymethyl)aminomethane salt of the molecule having the general formula
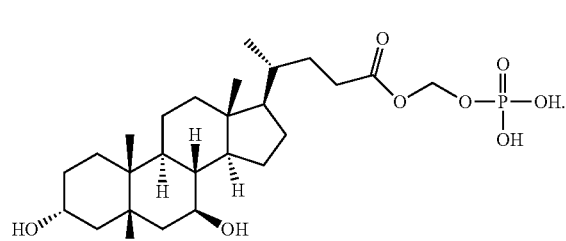
\* \* \* \* \*